(12) United States Patent
Bar-Cohen et al.

(10) Patent No.: US 6,247,367 B1
(45) Date of Patent: Jun. 19, 2001

(54) MULTIPLEXED ULTRASONIC SYSTEM

(75) Inventors: Yoseph Bar-Cohen, Seal Beach; Susan Kersey, Westminster; Cedric Daksla, Oxnard; Anatoly Blanovsky, Los Angeles, all of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/291,404

(22) Filed: Apr. 13, 1999

Related U.S. Application Data

(60) Provisional application No. 60/082,058, filed on Apr. 16, 1998.

(51) Int. Cl.[7] .................................................... G01P 29/04
(52) U.S. Cl. ................................. 73/628; 73/620; 73/641
(58) Field of Search .............................. 73/627, 628, 644, 73/641, DIG. 1, 629, 633, 582, 598, 620, 610, 624

(56) References Cited

U.S. PATENT DOCUMENTS

| | | | | |
|---|---|---|---|---|
| 4,305,297 | * | 12/1981 | Ries et al. | 73/628 |
| 4,457,174 | * | 7/1984 | Bar-Cohen et al. | 73/598 |
| 4,592,237 | * | 6/1986 | Ogura et al. | 73/602 |
| 4,674,334 | * | 6/1987 | Chimenti et al. | 73/627 |
| 4,976,150 | * | 12/1990 | Deka | 73/644 |
| 5,533,401 | * | 7/1996 | Gilmore | 73/628 |

* cited by examiner

*Primary Examiner*—Helen Kwok
(74) *Attorney, Agent, or Firm*—Fish & Richardson P.C.

(57) ABSTRACT

A system which rapidly determines the elastic stiffness constants of materials in plate shape as well as characterize material flaws that are affecting these constants. Rapid (below a minute) nondestructive evaluation system allow for the determination of material stiffness constants, low noise data acquisition algorithm for measuring spectral data. A real time method of displaying leaky Lamb wave spectral data.

7 Claims, 9 Drawing Sheets

MULTIPLEXED ULTRASONIC SYSTEM

CROSS REFERENCE TO RELATED APPLICATIONS

This application claims the benefit of the U.S. Provisional Application Nos. 60/082,058, filed on Apr. 16, 1998.

STATEMENT AS TO FEDERALLY SPONSORED RESEARCH

The invention described herein was made in the performance of work under a NASA contract, and is subject to the provisions of Public Law 96-517 (35 U.S.C. 202) in which the Contractor has elected to retain title.

BACKGROUND

Composite materials are increasingly being applied to aircraft, spacecraft, large space precision optics and various structural components. Reliable quantitative inspection methods can be used to determine the integrity and serviceability of composite structures. The elastic stiffness constants of composites determine the mechanical behavior and dimensional stability of the related structures. It is therefore important to determine these characteristics accurately.

Destructive tests are often used to determine the elastic properties of the material. These tests are expensive and can only be performed on representative samples, since the samples are eventually destroyed. On the other hand, nondestructive evaluation methods could be used to test each structure itself, rather than only testing a representative sample. Nondestructive evaluation can also be used to determine the status of an aging structure without removing it from service.

Attempts at nondestructive evaluation for material characterization of composites has so far met with limited success. The conventional pulse-echo and through-transmission tests are capable of yielding only one of the five stiffness constants of composites (transversely isotropic material behavior).

The leaky Lamb wave (LLW) technique, discovered by an inventor of this system, Yoseph Bar-Cohen, uses guided waves which propagate in parallel to the surface of the laminate. This has been shown to yield all the matrix-dominated constants. These constants are indicative of the quality of the material once the correct fibers are chosen.

The prior art leaky Lamb wave (LLW) test capability has also been slow, e.g. requiring about half an hour for each point. Other LLW techniques can lower this to a few minutes. The characterization of a test part requires scanning with steps that are as small as 1/16 inch. This can require millions of points to be characterized.

The LLW data acquisition process involves the acquisition of the reflected wave spectra at various angles of incidence. The amplitude is measured individually for signals in a preselected frequency range. Once this stage is complete, the minima, representing the plate wave modes, that appear on the reflected spectra for each given angle of incidence, are identified. These modes are recorded for the specific angle of incidence and converted to a phase velocity using Snell's law. The process of mode determination is continued for the range of incidence angles that is usually from 12.5° to 50° for graphite/epoxy composite material but may be different for other materials. The curve that is produced is known as the characteristic dispersion curve.

The dispersion curve represents the plate wave modes for the given direction with the fibers. It is useful to measure the dispersion curves for the 0°, 45° and 90° polar angles, measured with the first layer of the laminate, as a means of characterizing the laminate.

Once the dispersion data is available, an inversion technique is applied to determine the elastic stiffness constants. The method of inversion, is known in the art and described in Y. Bar-Cohen, A. K. Mal and S. Lih. "NDE of Composite Materials Uising Ultrasonic Oblique Insoniication." *Materiails Evaluation*, Vol. 51, No. 11, (Nov. 1993) 1285–1296). It has allowed determination of the properties based on data representing a single layer.

Another limitation occurs when testing multi-layered composites because of the large number of associated variables including each layer thickness, density and the presence of a rich epoxy layer at the interfaces.

SUMMARY

The present specification discloses a multiplexed setup that increases the speed of operation of the basic LLW system. This is done in a way that can serve as an add-on to commercially available ultrasonic inspection systems in order to increase the speed of said systems.

BRIEF DESCRIPTION OF THE DRAWINGS

These and other aspects of the invention will be described with reference to the accompanying drawings, in which.

DESCRIPTION OF THE PREFERRED EMBODIMENTS

Figure 1:
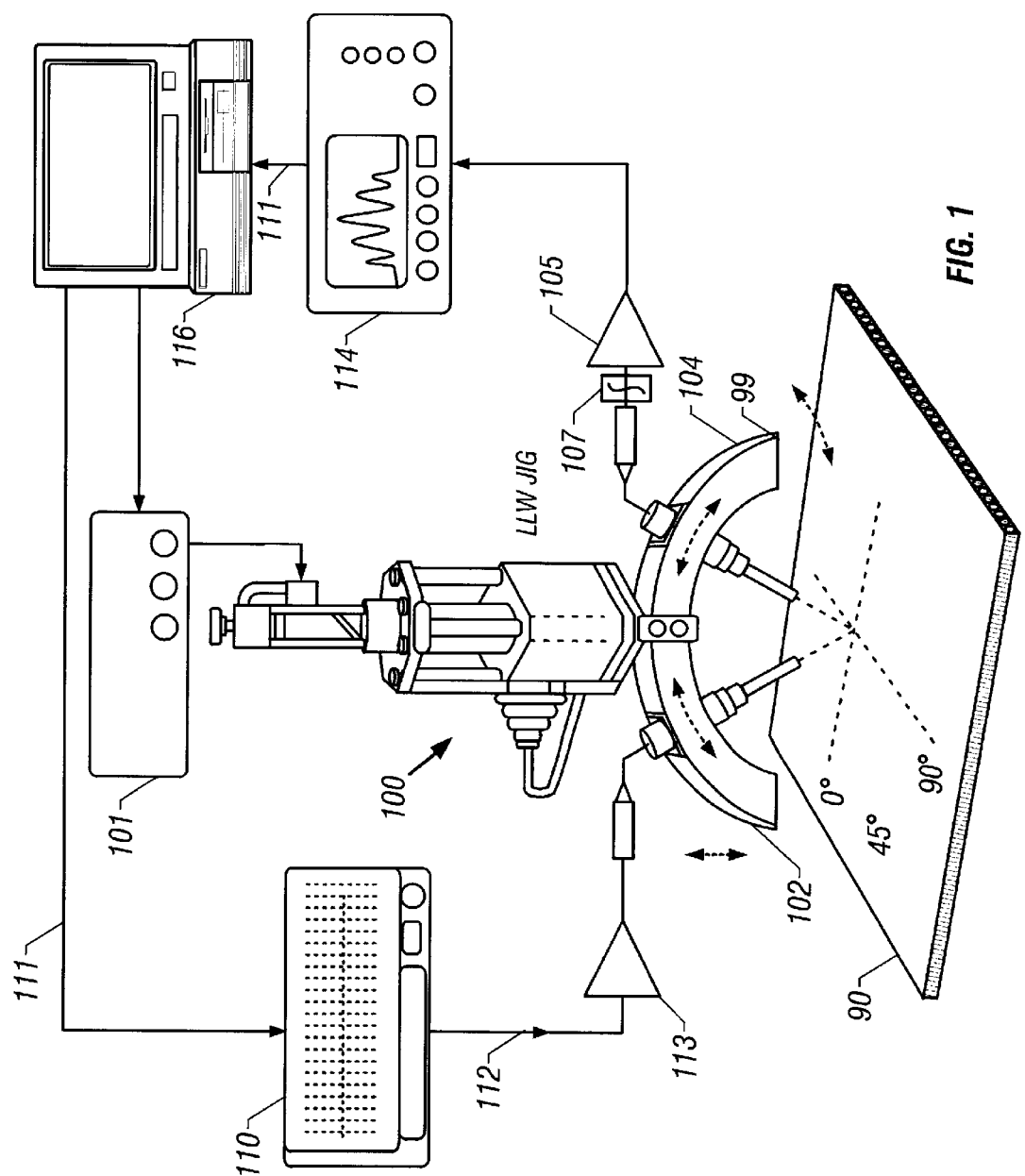
FIG. 1 shows a schematic view of a system.

An embodiment is shown in FIG. 1. This embodiment uses a function generator 110 to produce the drive 112 to the transducer transmitter 102. The output 112 of function generator 110 is amplified by amplifier 113 and coupled to transmitter 102. Transmitter 102 emits the beam to material 90, and the beam is reflected and received by receiver 104. The received output is amplified by amplifier 105 and coupled to scope 114 for display. A substantially arcuate shaped holder couples the transmitter and receiver 104 to one another.

Digital scope 114 acquires the responsive communication and couples that response to a personal computer 116 via IEEE-488 parallel interface as shown as 111.

The function generator 110 is used to produce a FM modulated sweep operation. Signals are transmitted that include sequentially-varying frequency tone-bursts. The received signal represents spectral data in the time domain which can be directly displayed on any scope without Fourier analysis. The received reflection spectrum has low frequency characteristics. Therefore, high frequency noise, which might otherwise interfere with the measured spectrum, is filtered by filter 107 to reduce noise. The filtered signals are amplified by amplifier 105.

The LLW scanner 100, including transmitter 102 and receiver 104, is controlled by control hardware 101. The control system controls the height, rotation angle and the angle of incidence of transducer assembly 99. A control system of the computer automatically sets the height of the transducer pair—transmitter 102 and receiver 104—by finding the optimum position where the receiver 104 is placed at the null zone of the leaky Lamb waves.

This is done by treating the acquired reflected spectrum as a statistical distribution function. The computer automatically determines the proper height by varying the height and finding an optimum height where maximum consecutive standard deviation is obtained.

This compares with the prior art systems where the height is searched manually by the operator who visually identifies the location at which the highest peak amplitude is observed with the lowest minima of the LLW modes. This requires substantial skill and training. As a result, the existing approach was not user friendly and led to data inconsistency caused by operator error.

Figure 2:
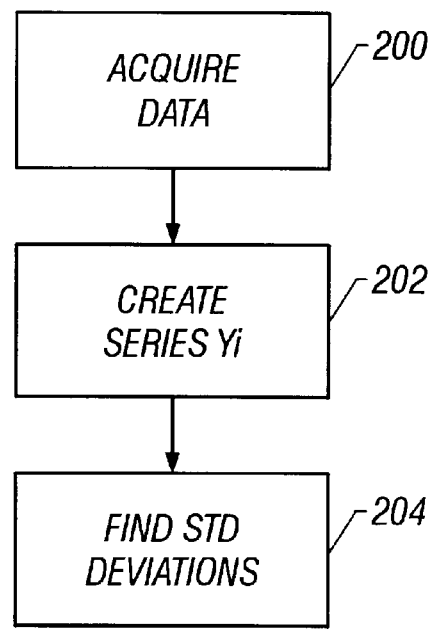
FIG. 2 shows a flowchart of operation.

The procedure for the automatic height adjustment technique is described with reference to the flowchart of FIG. 2.

Assume that there is a total set of n raw data, $x_1$ to $x_n$, representing the amplitudes of a signal in the frequency domain. This data is acquired at step 200. Since the contrast between the minima and the adjacent points is important, a series $y_i=(x_{i+1}-x_i)$, i=1 to n-1 is created at step 202. The standard deviation of this new series is used as an indication for adjustment of the transducer height. The location at which the maximum standard deviation, s, is obtained is derived as follows, $$s = \sqrt{\frac{\sum_{i=1}^{n-1}(y_i - \bar{y})^2}{n-2}}$$

where $\bar{y}$ is the mean value of the series $y_i$, i=1 to n-1. Considering that the series $x_i$ starts and ends both at zero, the mean value of the series $y_i=(x_{i+1}-x_i)$, i=1 to n-1, must be zero. So the standard deviation becomes, $$s = \sqrt{\frac{\sum_{i=1}^{n-1} y_i^2}{n-2}} = \sqrt{\frac{\sum_{i=1}^{n-1}(x_{i+1}-x_i)^2}{n-2}}$$

$$= \sqrt{\frac{\sum_{i=1}^{n-1}(x_{i-1}^2 - 2x_{i+1}x_i + x_i^2)}{n-2}}$$

$$= \sqrt{\frac{2\sum_{i=1}^{n-1} x_i^2 - 2\sum_{i=1}^{n-1}(x_{i+1}x_i)}{n-2}}$$

s values are recorded and the maximum is searched while the height of the LLW setup is changed up and down around the expected value.

Figure 3:
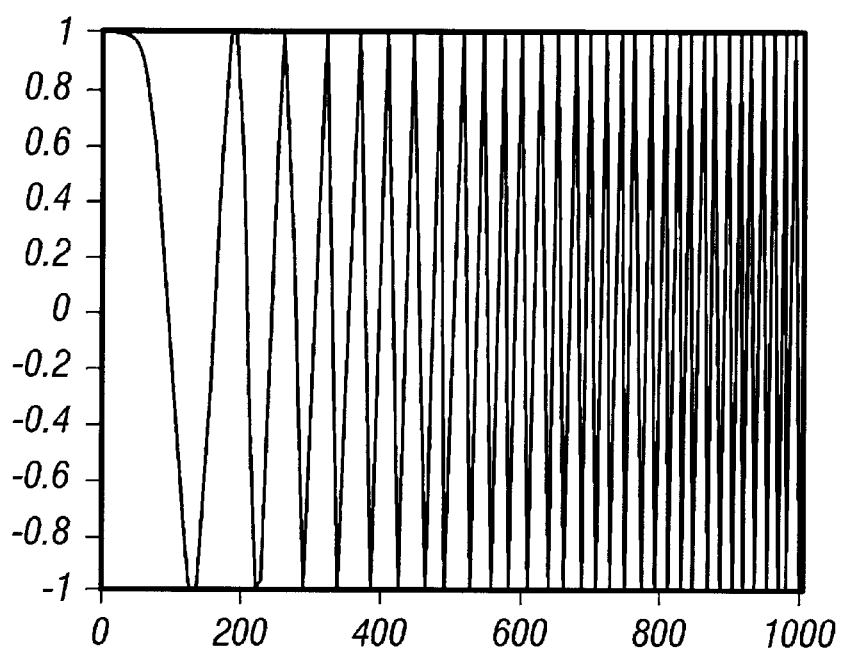
FIG. 3 shows an FM modulated insonification signal.

The control of the incidence angle allows simultaneously changing of the transmitter and receiver angle while maintaining a pivot point on the part surface and assuring accurate measurement of the reflected ultrasonic signals. The FM function is expressed as $$FRQ = STA \times (1+K)^N$$

where FRQ is the frequency value, STA is the starting frequency of the frequency-sweep signal, K and N are functions of the sweep time. The preferred setup uses the values K=0.015625 and N=149. The start and stop frequency of the frequency-sweep signal is 1 MHz and 10 MHz, respectively. This generator also provides a reference frequency marker for the calibration of the data acquisition when converting the scale of the signal x-axis from time to frequency domain as shown in FIG. 3.

The preferred embodiment uses digital scope 114 to acquire the reflection spectral data after it is amplified and filtered. To produce an integrated system with faster operation, this data acquisition can be miniaturized and compacted to reside on a single electronic board of a personal computer. Originally, the acquisition of the LLW modes was a single tone-burst frequency at a time at each angle of incidence. This step is eliminated in this system. The program controls the LLW scanner to start it from the home position at which the transducers are at known coordinates, e.g. the origin (0,0). The starting angle is set to 12.5 in the current system.

Figure 4:
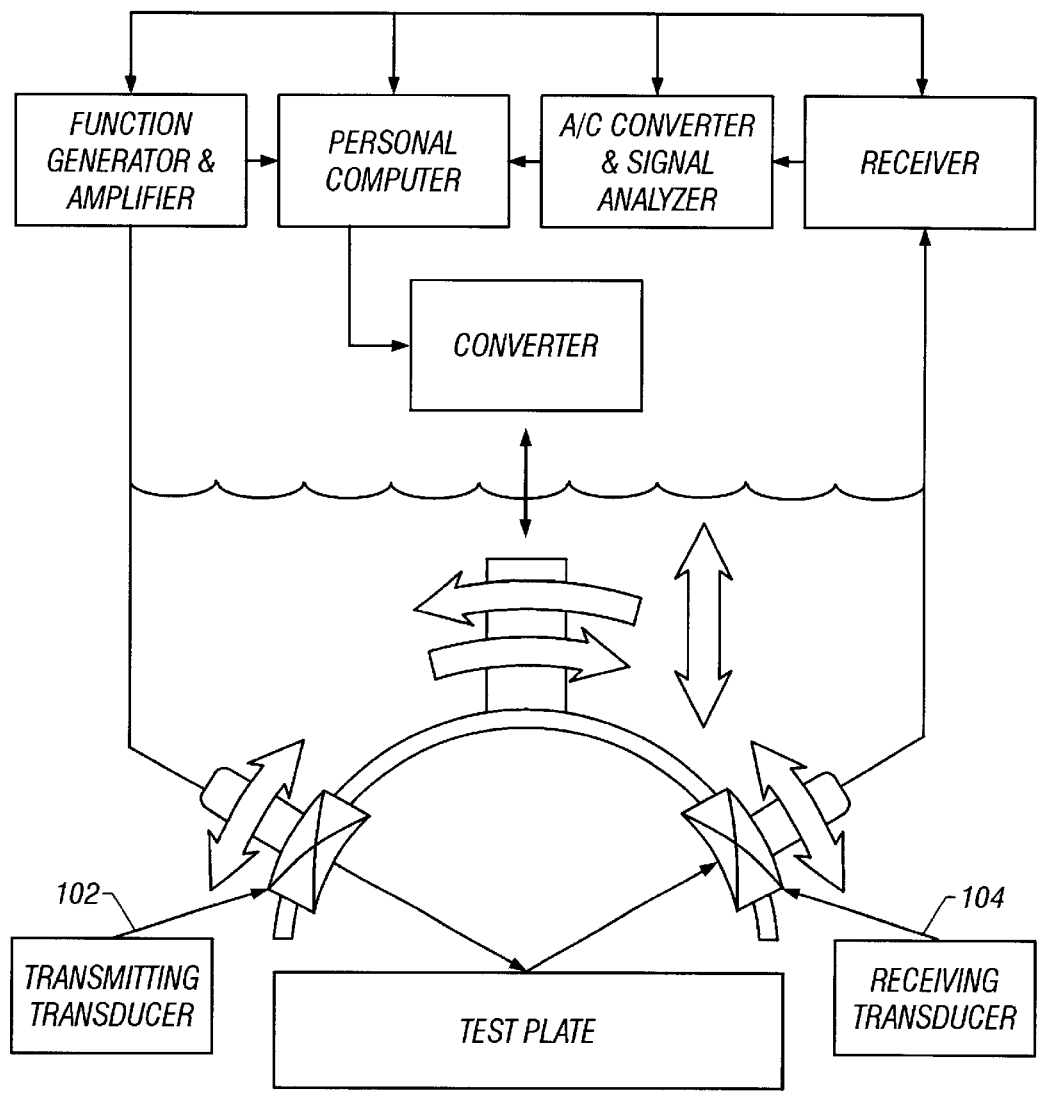
FIG. 4 shows a schematic diagram of the data acquisition system.

The data acquisition block diagram is shown in FIG. 4. The signals that are induced by the transmitter are shown being received, processed and analyzed by a personal computer after being digitized.

A user selectable menu provides an improved user allowing the selection of the desired test options. These options include setting up the system as well as preparing it for data acquisition and later performing the inversion analysis.

Figure 5:
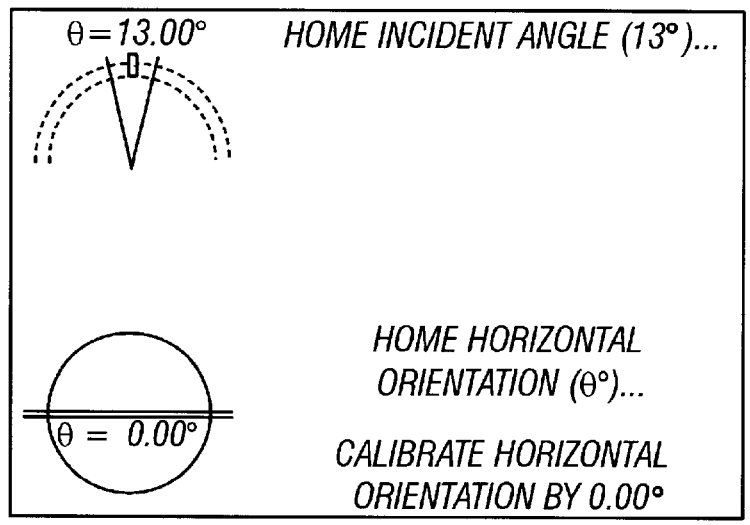
FIG. 5 shows a view of the computer display at the stage of system homing.

The processor begins by setting the LLW scanner at its home position. This includes placing the receivers at 12.5° and the scanner plan along the fibers of the composite laminate. The system moves the probes and the fixture in a sequence of travel that allows finding the location of the limit switches where the motion stops. That location is identified as a home coordinate. The home positioning is important since it allows the system to operate without an encoder in an open loop mode and it is essential to find the home to determine the location of the transducers during the data acquisition process. The operator receives a computer display feedback of this operation as shown in FIG. 5.

Figure 6A:
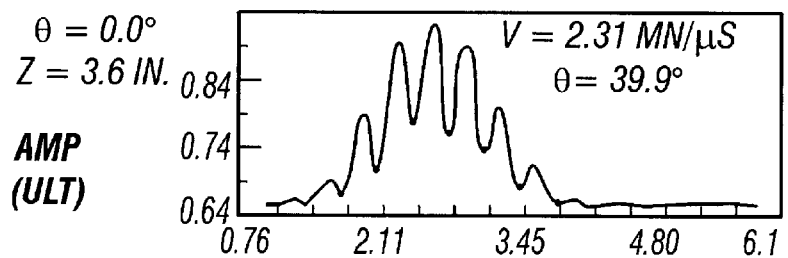
FIG. 6 shows a view of the acquired data for a given angle of incidence (39.9°) during the acquisition of the dispersion curve, where the top section shows the reflection spectrum, the computer marks the minima associated with the plate wave modes and the bottom shows the accumulating data on the dispersion curve.
Figure 6B:
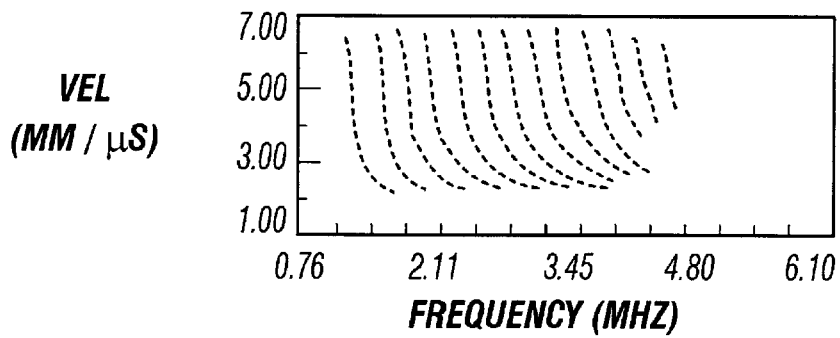

Once this stage is complete, the computer starts the data acquisition process. At each of the selected angles of incidence, the reflection spectrum is acquired and the location of the minima (LLW modes) is identified and marked on the reflection spectrum. These minima are accumulated on the dispersion curve, which is shown on the lower part of the display as shown in FIG. 6. The inventor's experiments have shown that the process of acquiring a dispersion curve for 20 different angles of incidence takes less than 45 seconds. This is significantly faster that the current 15–30 minute process.

Figure 7:
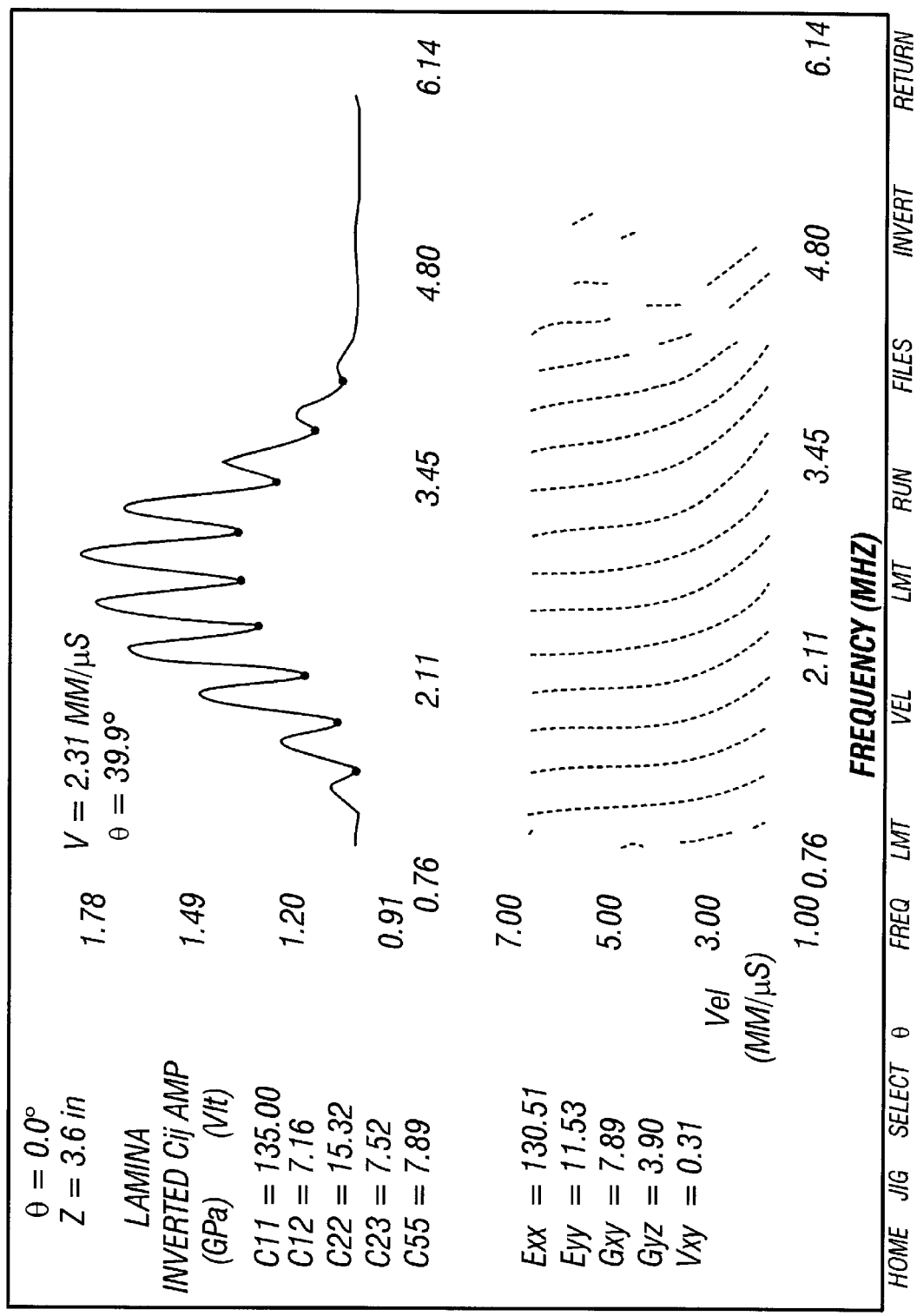
FIG. 7 shows a view of the screen after the completion of the data acquisition phase and the data inversion. The elastic stiffness constants are inverted from the dispersion curve and are presented as a list on the left.

Once the dispersion data is ready, the inversion option of the software is activated and the elastic stiffness constants are determined and presented on the display as shown in FIG. 7. The inversion is an analytical process which seeks the stiffness constants which form a best fit between the measurements and the analytical predictions.

To enhance the accuracy of the inversion of the material stiffness constants, dispersion curves can be acquired in the form of a detailed image. The image x-axis shows the frequency, the y-axis shows the phase velocity and each of the pixels of the image has a color or a shade of gray that represents the amplitude of the reflection spectrum at the given phase velocity (i.e., angle of incidence). A color or shades of gray scale lookup table on the computer monitor allows the user to view the level of the reflection amplitude at the given frequency and phase velocity.

Figure 8:
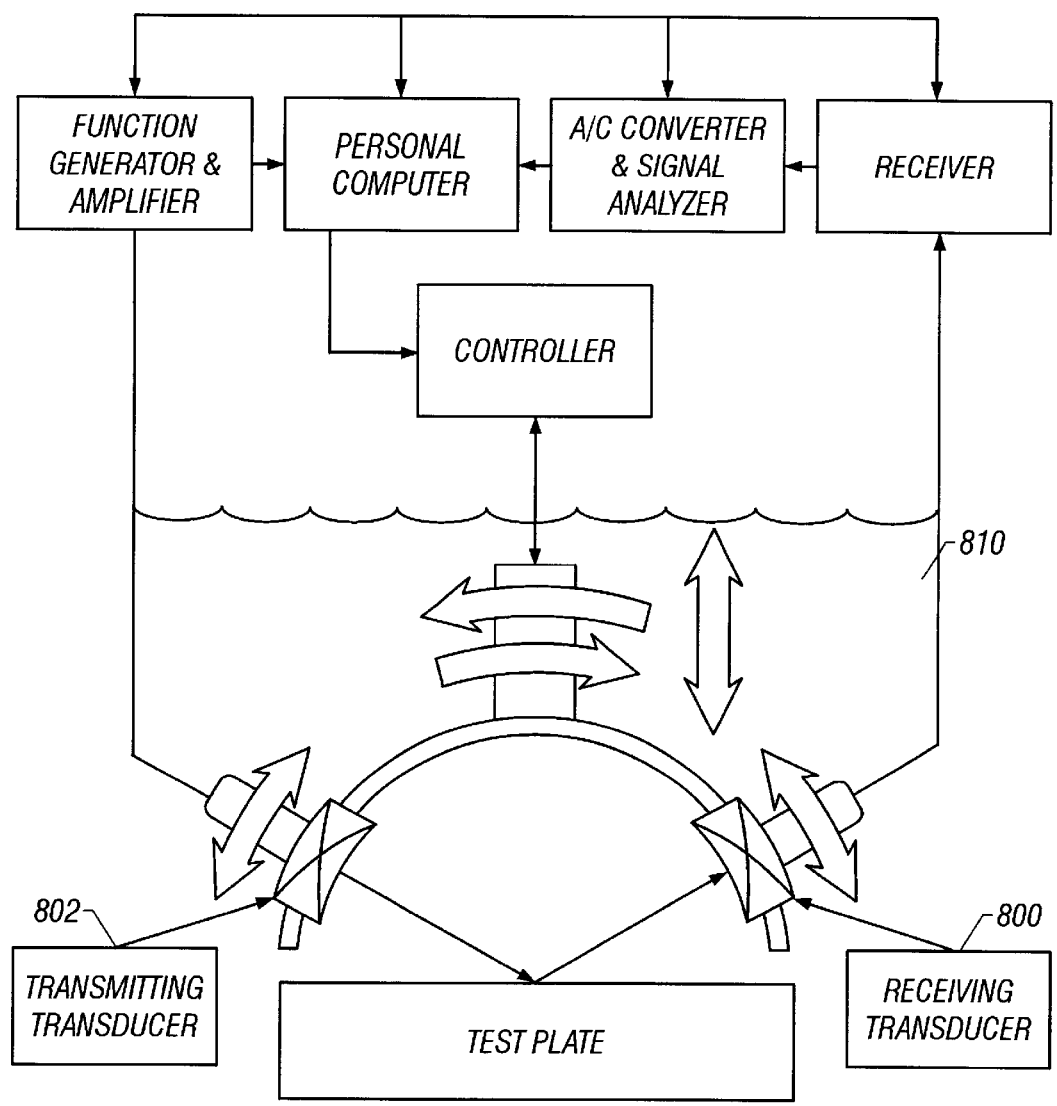
FIG. 8 shows a view of the LLW setup with schematic diagram of the test setup of the multiplexed embodiment.

An improved embodiment is shown in FIG. 8. In this embodiment, it is recognized that the leaky Lamb wave data is produced slowly because of the large number of test points that are acquired during a practical ultrasonic scanning process. The system uses a pair of transducers 800, 802, placed in a pitch-catch arrangement, which is an arrangement in which one transducer sends the wave onto the part; and the other transducer in the pair receives the reflection.

Systems such as those used in FIG. 1 mechanically change the angle of incidence of the ultrasonic wave over a selected range. As described above, these were recorded to form an accumulated dispersion curve. In this system shown in FIG. 8, however, the pair of pitch-catch transducers can remove at least some of this necessity.

Figure 9:
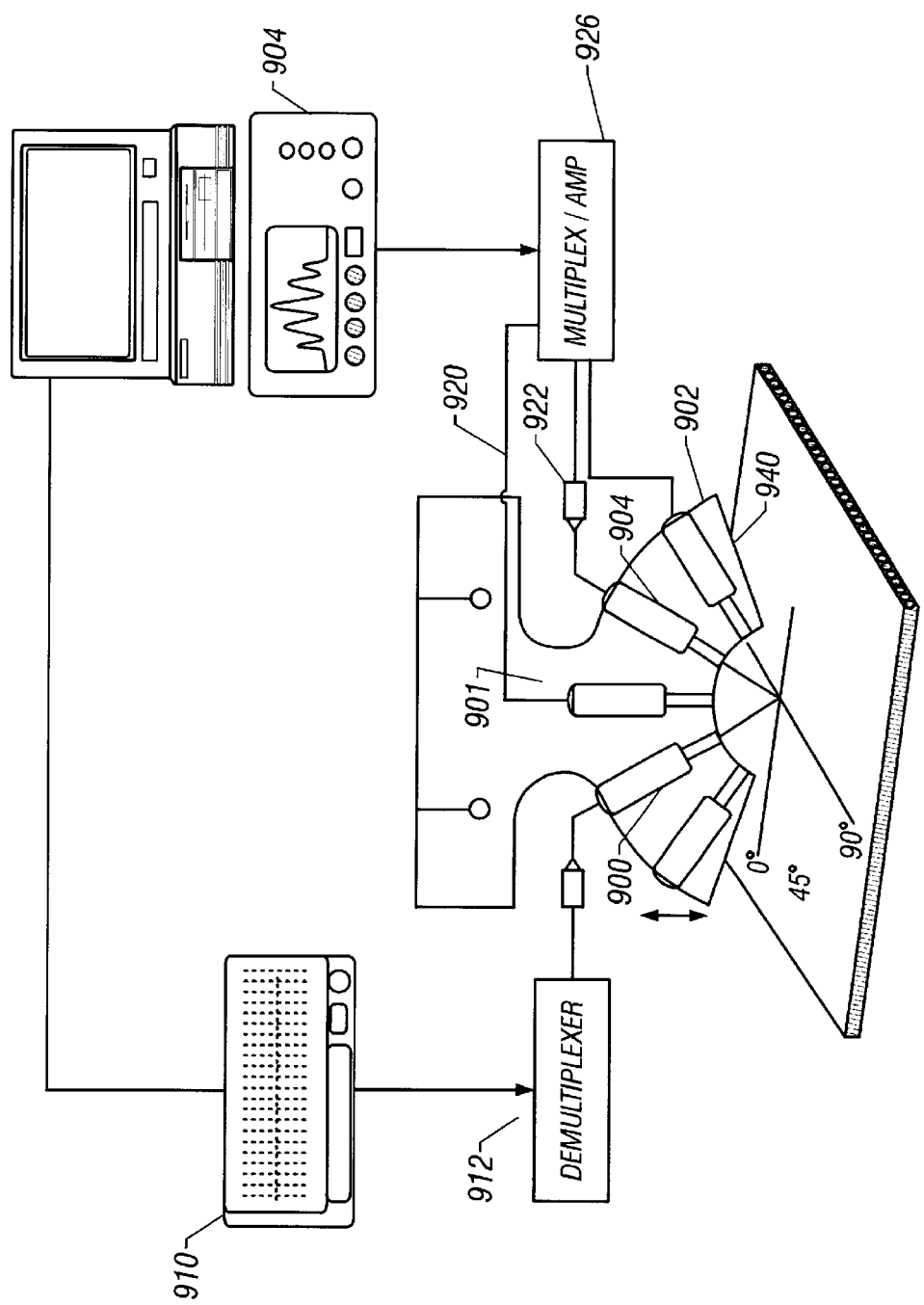
FIG. 9 shows the block diagram of the multiplexed embodiment.
Figure 11:
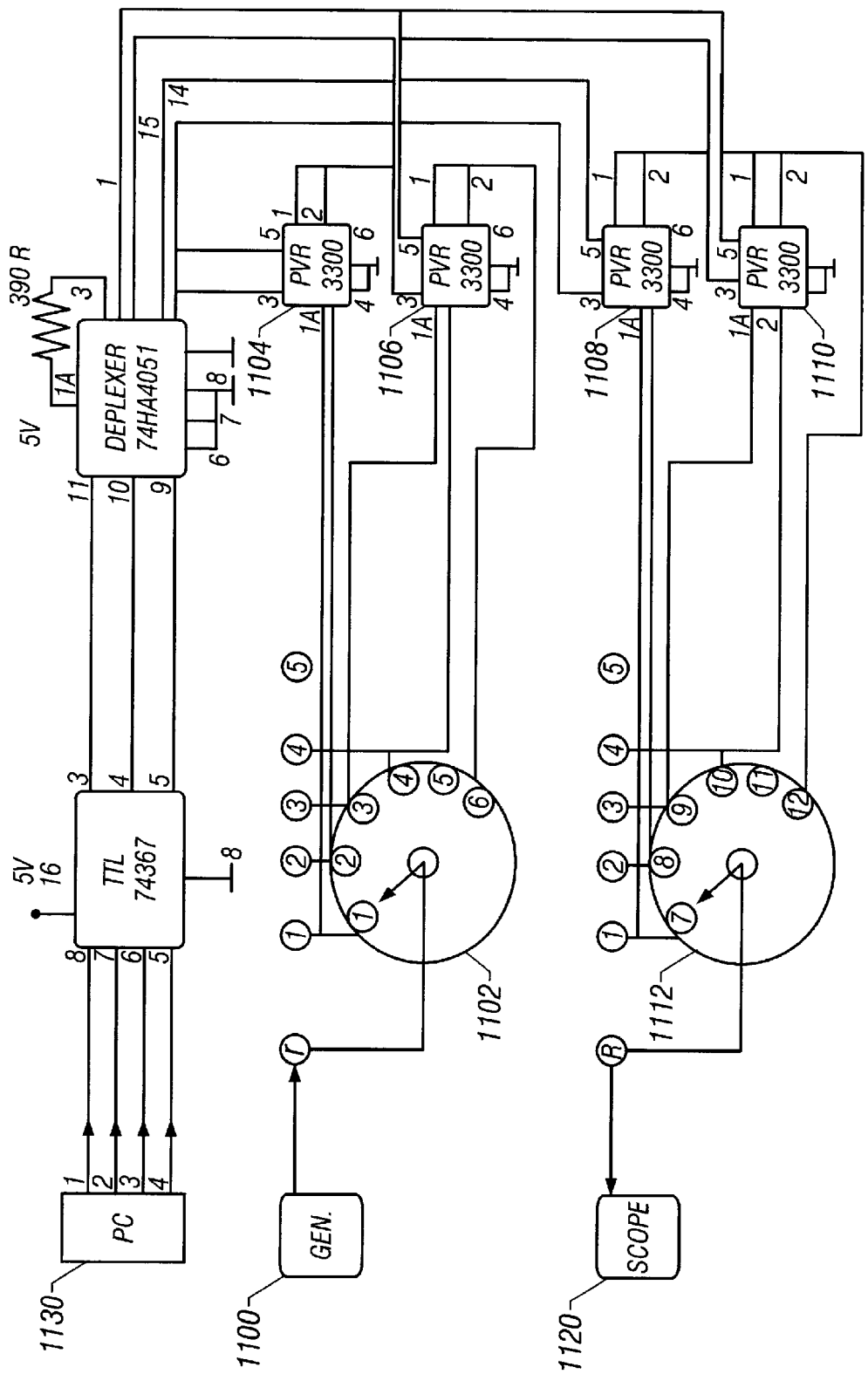
FIG. 11 shows a schematic diagram of the multiplexer system.

FIG. 9 shows a block diagram using multiple pairs of transducers. Signals that are induced by each transmitter, e.g. 900, and received by each receiver, e.g. 902. Those received signals are received, processed, and analyzed by a personal computer 904 in the conventional way. The system activates sequentially the various pairs of transducers using the multiplexer, and electronically scans the incident angle range by scanning across the multiplexer 912 and demultiplexer 926. As in the first embodiment, a function generator 910 drivers the transmitters through multiplexer 912. FIG. 11 describes how the signal is applied to different transmitters at different times, without moving the support 901 that holds all the transmitters and receivers.

The inventors realized that much of the time for the measurement was, in the past, taken by physically moving the support 901, to get the different angles. In this system, information from a number of angles are obtained from each position of the transducer support.

By adding a number of additional transducers in this system, it becomes possible to increase the speed of obtaining the data. For example, the system in FIG. 9 shows two transmitters and three receivers. Three sets of information are therefore obtained for each position of the support. By using this information from all three of the receivers, it should be seen that a number of different angular pieces of information can be obtained without moving the support. Each of the different receptions corresponds to a different angle reflection. These different receptions, 920, 922, 924, are multiplexed and amplified by amplifier/demultiplexer 926. The composite material can hence be done more expediently.

The standard computer program used for the previous systems are used. The program displays a user menu that controls the data acquisition and analysis operation. This computer program may be modified to control automatically the sequence the selected transducer pair to allow acquiring the material dispersion curve. Each pair represents a given angle of incidence and the acquired data is display on the screen. The locations of the minima (LLW Modes) on the spectra are marked by the computer and are accumulated separately to form a dispersion curve. An example of a typical reflection spectrum. The acquired dispersion curve is therefore obtained. Once the dispersion data is ready, the software option of data inversion is activated and the elastic stiffness constants are determined. The inversion is an analytical process, which seeks the stiffness constants best on a best fit between the measurements and the analytical predictions.

The preferred system uses four pairs of 5 MHz transducers. The transducers are mounted on a plexiglass transducer holder shown in FIG. 10, that holds the transducers relative to one another. The spectral range sets the center frequency of the transducer pairs.

Figure 10:
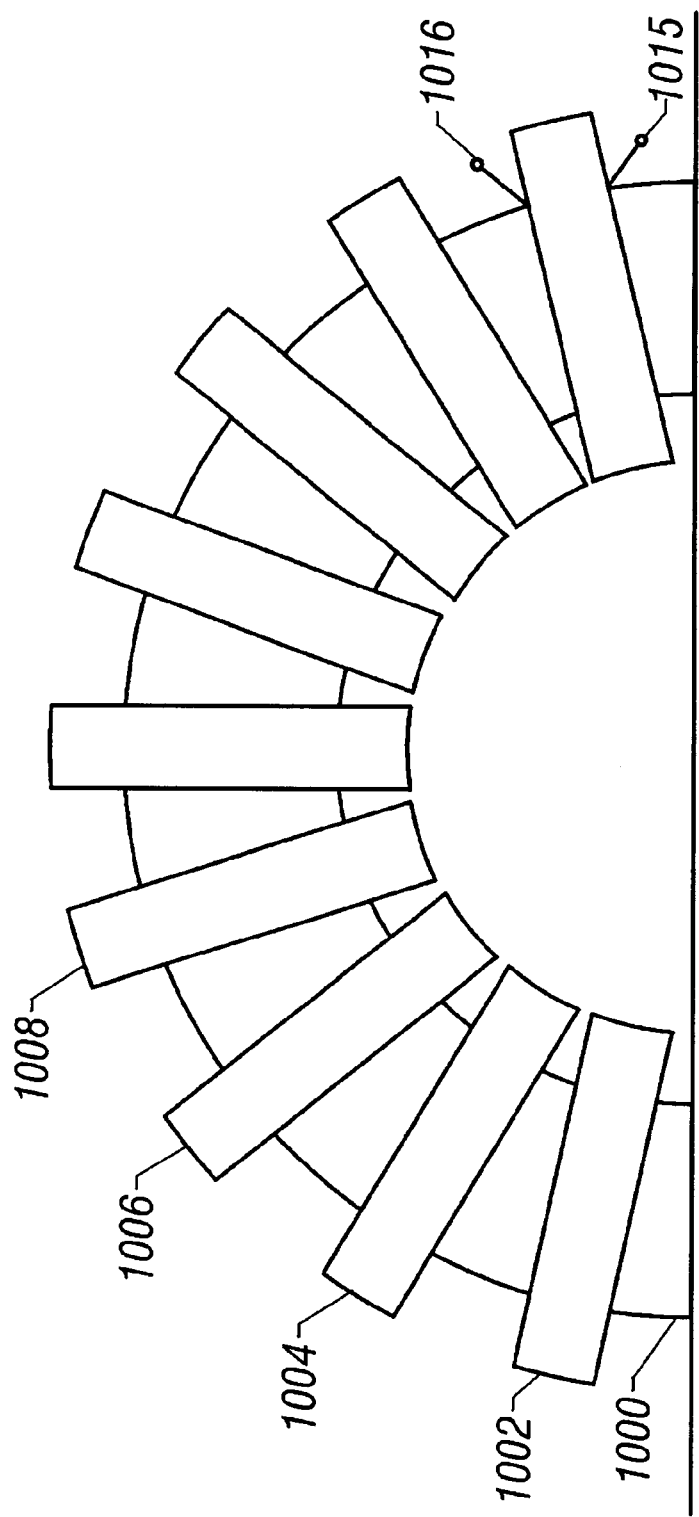
FIG. 10 shows a diagram of the multiplexer jig.

The preferred transducer in FIG. 10 shows four transducer pairs aligned to transmit at 15, 30, 45, and 60° angles of incidence, shown as transducers 1002, 1004, 1006 and 1008 respectively. This can be used to acquire a dispersion curve with a total of all phase velocities corresponding to the angles of incidence through Snell's law. Two additional dispersion curves at 45 and 90° may also be used if necessary to acquire a full material characterization. The mount 1000 is preferably formed of plexiglass material that is also fixtured to allow small corrections of the angle of incidence and to achieve pitch-catch arrangement. FIG. 10 shows the adjustment screws 1015, 1016 to carry out the adjustment.

The system is shown in FIG. 8 as being mounted in a water tank, using water 810 to provide the ultrasonic coupling medium.

FIG. 11 shows a detailed electrical connection diagram of the multiplexer 926 system, shown in block form in FIG. 9. This multiplexer controls the selected transducer pair in order to trigger the data acquisition. A pulse generator 1100, preferably a Hewlett-Packard 8116A, drivers an electrically selectable rotary switch 1102 whose output is connected to the different transducer transmitters 1104, 1106. Only two transducers are shown for clarity, but it should be understood that others could be alternately used. The reception is similarly obtained by the receivers 1108, 1110 which are coupled to the output through another electrically controlled rotary switch 1112 whose position is synchronized with the position of the switch 1102. The output is connected to a digital scope 1120, preferably a LeCroy 9410 series dual 150 MHz scope. This displays the reflection spectrum in real time. The output is also connected through circuitry, which activates the selected pair of transducers that would be operated at any given moment, to a personal computer 1130 that controls the data acquisition and display, determines the accumulated dispersion curve, and inverts the elastic properties as described above. Since multiple angular measurements can be obtained at a single position of the jig, a dispersion curve with four angles of incidence can be done in 7.4 seconds.

Other embodiments are within the disclosed embodiments.

What is claimed is:
1. A material characterization device, comprising:
a fixture, having a surface with an arcuate shape, holding a plurality of ultrasonic transducers on said arcuate shape at specified angles relative to one another, said fixture including a plurality of transmitter transducers, and a plurality of receiver transducers;
a multiplexing arrangement, which drives the transmitter transducers and receives input from the receiver transducers, to enable obtaining information from a plurality of angles of incidences from a single position of said fixture; and a leaky Lamb wave processing element, receiving said information, and processing said information from said plurality of angles of incidences to obtain a plurality of information sets without moving said fixture.

2. A system as in claim 1 wherein said fixture includes a plurality of inner surfaces holding said ultrasonic transducers at angles of 15, 30 and 45 degrees relative to the horizontal.

3. A device as in claim 1 wherein said multiplexing arrangement comprises a plurality of switches which are driven synchronously relative to one another.

4. A device as in claim 3 wherein said switches are rotary switches whose positions are electrically controllable.

5. A device as in claim 4 further comprising a computer program which analyzes information from each of the positions.

6. A device as in claim 4 further comprising a computer, programmed to receive reflections from each of said receiver transducers, one after another, and to use all of said information to provide information indicating characterization of a material.

7. A method of characterizing a material, comprising:

attaching a plurality of ultrasonic transducers onto a shaped test fixture, said attaching includes coupling each of said plurality of transducers to specified portions on a an arcuate shaped surface of said fixture at a plurality of predetermined plurality of positions, said angular transducers including a plurality of transmitters and a plurality of receivers, each one receiver associated with one transmitter, and arranged to receive a reflection with one transmitter, and arranged to receive a reflection therefrom; and obtaining a plurality of items of information indicating a plurality of different angles of incidence on a material, without moving said fixture.

* * * * *